US010111952B2

(12) United States Patent
Weigandt et al.

(10) Patent No.: US 10,111,952 B2
(45) Date of Patent: *Oct. 30, 2018

(54) SILICON DIOXIDE NANOPARTICLES AND THE USE THEREOF FOR VACCINATION

(71) Applicant: Merck Patent GmbH, Darmstadt (DE)

(72) Inventors: Markus Weigandt, Mannheim (DE); Andrea Hanefeld, Heidelberg (DE); Armin Kuebelbeck, Bensheim (DE); Gregor Larbig, Gelnhausen (DE)

(73) Assignee: MERCK PATENT GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,665

(22) Filed: Oct. 6, 2017

(65) Prior Publication Data

US 2018/0071386 A1    Mar. 15, 2018

Related U.S. Application Data

(62) Division of application No. 15/197,870, filed on Jun. 30, 2016, now Pat. No. 9,808,521, which is a division of application No. 14/611,891, filed on Feb. 2, 2015, now Pat. No. 9,433,673, which is a division of application No. 13/054,169, filed as application No. PCT/EP2009/005078 on Jul. 13, 2009, now Pat. No. 8,980,324.

(30) Foreign Application Priority Data

Jul. 15, 2008   (DE) .................. 10 2008 033 175

(51) Int. Cl.
A61K 39/39 (2006.01)
A61K 9/00 (2006.01)
A61K 9/51 (2006.01)
B82Y 5/00 (2011.01)
A61K 39/00 (2006.01)
A61K 9/10 (2006.01)
A61K 9/14 (2006.01)
A61K 47/52 (2017.01)
A61K 47/54 (2017.01)
A61K 47/64 (2017.01)
A61K 47/69 (2017.01)

(52) U.S. Cl.
CPC ............ A61K 39/39 (2013.01); A61K 9/0019 (2013.01); A61K 9/10 (2013.01); A61K 9/143 (2013.01); A61K 9/5115 (2013.01); A61K 39/0005 (2013.01); A61K 47/52 (2017.08); A61K 47/54 (2017.08); A61K 47/643 (2017.08); A61K 47/6923 (2017.08); B82Y 5/00 (2013.01); A61K 2039/55505 (2013.01); A61K 2039/62 (2013.01); Y10T 428/2982 (2015.01)

(58) Field of Classification Search
CPC .. A61K 39/39; A61K 39/0005; A61K 9/0019; A61K 9/5115; A61K 9/10; A61K 9/143; A61K 47/52; A61K 47/54; A61K 47/643
See application file for complete search history.

(56) References Cited

U.S. PATENT DOCUMENTS

| 6,086,881 A | 7/2000 | Frey et al. |
| 7,332,586 B2 | 2/2008 | Franzen et al. |
| 2006/0251726 A1 | 11/2006 | Lin et al. |
| 2007/0292518 A1 | 12/2007 | Ludwig |
| 2008/0286371 A1 | 11/2008 | Pacheco et al. |
| 2009/0155292 A1 | 6/2009 | Santamaria et al. |
| 2012/0021056 A1 | 1/2012 | West et al. |

FOREIGN PATENT DOCUMENTS

| EP | 0216278 A2 | 4/1987 |
| EP | 0216278 B1 | 4/1987 |
| EP | 0465081 B1 | 1/1992 |
| JP | 2004-508301 A | 3/2004 |
| JP | 2004-138522 A | 5/2004 |
| JP | 2006335722 A | 12/2006 |
| JP | 2008-515385 A | 5/2008 |
| WO | 9529701 A | 11/1995 |
| WO | 0112221 A1 | 2/2001 |
| WO | 2004108072 A2 | 12/2004 |
| WO | 2005085135 A1 | 9/2005 |
| WO | 2007030901 A | 3/2007 |

(Continued)

OTHER PUBLICATIONS

Wildermann et al. Human Vaccines and immunotherapeutics 12(1); 239-243 (2016).*
Jacobset al. Anticancer Research 2689-2700.*
English language Abstract for corresponding Japanese Application No. 2004-138522, published May 13, 2004.
English language Abstract for corresponding Japanese Application No. 2004-508301, pubished Mar. 18, 2004.
English language Abstract for corresponding Japanese Application No. 2008-515385, published May 15, 2008.
Haag et al., "Polymere Therapeutika: Konzepte und Anwendungen", Angew. Chem., (2006), vol. 118, pp. 1218-1237.

(Continued)

Primary Examiner — Shirley V Gembeh
(74) Attorney, Agent, or Firm — Millen, White, Zelano & Branigan, P.C.

(57) ABSTRACT

The invention relates to ultrasmall, monodisperse nanoparticles comprising silicon dioxide to the surface of which at least one antigen is attached. The nanoparticles can be used for the immunoprophylaxis or immunotherapy of cancer. The invention also relates to a method for the targeting of antigens at antigen-presenting cells and for the activation of the immune system, where the efficiency of targeting and/or immunoactivation are set via the particle characteristics. The invention also relates to a method for the active and passive immunisation of a mammal.

28 Claims, 4 Drawing Sheets

(56) References Cited

FOREIGN PATENT DOCUMENTS

WO  2007039192 A2  4/2007
WO  2008109366 A2  9/2008

OTHER PUBLICATIONS

K. B. Sharpless, Angew. Chem. Int. Ed., (2001), vol. 40, pp. 2004-2021.
Stober et al., "Controlled Growth of Monodisperse Silica Spheres in the Micron Size Range", Journal of Colloid and Interface Science, (1968), vol. 26, pp. 62-69.
Van Der Voort et al., "Silylation of the Silica Surface a Review", J. Liq. Chrom. & Rel. Technol., (1996), vol. 19, Nos. 17 & 18, pp. 2723-2752.
D. Mancino et al., "Adjuvant Effects of Amorphous Silica and of Aluminium Hudroxide on IgE and IgG1, Antibody Production in Different Inbred Mouse Strains", Int. Archs. Allergy appl. Immun., vol. 61, (1980), pp. 253-258.
Patricia L. Mottram et al., "Type 1 and 2 Immunity Following Vaccination is Influenced by Nanopartide Size: Formulation of a Model Vaccine for Respiratory Synctial Virus", Molecular Pharmaceutics, (2006), pp. 1-12.
International Search Report corresponding to PCT/EP2009/005078, dated Mar. 8, 2010.
Jain T K et al: "Nanometer silica particles encapsulating active compound: A novel ceramic drug carrier," Journal of the American Chemical Society 19981104 US Bd. 120, Nr. 43, Nov. 4, 1998, pp. 11092-11095, XP002562317 ISSN: 0002-7863.
Kreuter J Ed-Powell M Y et al: "Nanoparticles as Adjuvants for Vaccines" Vaccines Design.Submit and Adjuvant Approach: Pharmaceutical Biotechnology M New York, Plenum Press, US. vol. 6, No. 1, Jan. 1, 1995, pp. 463-472, XP001006942.
Chen J-F et al: "Preparation and Characterization of Porous Hollow Silica Nanoparticles for Drug Delivery Application," Biomaterials, Elsevier Science Publishers BV,. Barking,GB. vol. 24, No. 4, Feb. 1, 2004, pp. 723-727, XP004471063.
Reddy Sai T et al: "Exploiting Lymphatic Transport and Complement Activation in Nanoparticle Vaccines," Nature Biotechnology, vol. 25, No. 10, Oct. 2007, pp. 1159-1164, XP002568453.
Vallhov Helen et al: "Mesoporous Silica Particles Induce Size Dependent Effects on Human Dendritic Cells," Nano Letters Dec. 2007, vol. 7, No. 12, Dec. 2007, pp. 3576-3582, XP002532318.
Breitinger H-G: "Synthesis of silica-bound amylase by phosphorolytic elongation of immobilised maltohetaosyl hydrazides," Tetrahedron Letters, Elsevier, Amsterdam, Bd. 43, Nr. 35, Aug. 26, 2002, pp. 6127-6131, XP004373255, ISSN: 0040-4039.
Emerich et al., Journal of Drug Targeting, Apr. 2007, vol. 15, No. 3, pp. 163-183.

\* cited by examiner

SILICON DIOXIDE NANOPARTICLES AND THE USE THEREOF FOR VACCINATION

The invention relates to ultrasmall, monodisperse nanoparticles comprising silicon dioxide to the surface of which at least one antigen is attached. The nanoparticles can be used for the immunoprophylaxis or immunotherapy of cancer. The invention also relates to a method for the targeting of antigens at antigen-presenting cells and for the activation of the immune system, where the efficiency of targeting and/or immunoactivation are set via the particle characteristics. The invention also relates to a method for the active and passive immunisation of a mammal.

The health of an animal or human organism depends, inter alia, on the extent to which the organism is able to protect itself against pathogenic agents from its environment or the extent to which the organism is able to recognise and eliminate modified endogenous material. The immune system of the human or animal body, which carries out these functions, can be divided into two functional areas: the innate immune system and the acquired immune system. Innate immunity is the first line of defence against infections, and most potential pathogens are rendered harmless before they are able to cause, for example, detectable infection. The acquired immune system reacts to surface structures of the ingressing organism or the modified endogenous material, which are known as antigens.

There are two types of acquired immune responses: the humoral immune response and the cell-mediated immune response. In the humoral immune response, antibodies present in the body fluids bind to antigens and initiate deactivation thereof. In the cell-mediated immune response, T-cells, which are able to destroy other cells, become active. If, for example, proteins associated with a disease are present in a cell, they are fragmented proteolytically within the cell to give peptides. Specific cell proteins then bind to the resultant fragments of the protein or antigen and transport the latter to the surface of the cell, where they are presented to the molecular defence mechanisms, in particular T-cells of the body.

The molecules which transport the peptides to the cell surface and present them there are known as proteins of the major histocompatibility complex (MHC). The importance of MHC proteins also consists in that they enable T-cells to differentiate self antigens from non-self antigens. Knowledge of the sequence of a non-self peptide of this type enables the immune system to manipulate against diseased cells, for example using peptide vaccines.

Technologies for the presentation of proteinogenic or peptidic antigens in the area of vaccines must do two fundamental jobs: efficient transport of the antigen to dendritic cells and subsequent activation thereof in order to bring about an acquired immune response. Current vaccine development is focused on molecular strategies which address peripheral dendritic cells, such as, for example, in the skin or muscles, as target. The antigens are directed to their dendritic destination by, in particular, antibodies which are specific for cell surface receptors of the dendritic cells and are either fused to antigens or attached to particle surfaces. However, such demanding designs of the cell-specific targeting are not necessary, as was shown by, inter alia, Fifis et al. (2004) J Immunol. 173(5), 3148, who caused an immune response by the transport of silver-conjugated polystyrene beads to dendritic cells.

It is furthermore known in immunology to employ adjuvants in order to increase the immune response to a given substance non-specifically. Thus, whereas the antigen causes the specific immune response, the adjuvant is essentially responsible for the strength of this response. In order to cause an acquired immune response, the use of adjuvants is vital for the induction of dendritic cell maturation. Dendritic cells ripen here as a result of molecular danger signals, which act via signalling pathways of the connatal immunity, such as, for example, Toll-like receptors (TLRs) or inflammatory cytokine receptors. WO 2004/108072 A2, for example, describes a conjugate in which compounds which modify the immune response, such as, for example, TLR agonists, are bound to a metallic particle support, which in addition comprises at least one active compound. Compounds which modify the immune response should be regarded here as adjuvants for vaccines, which, although causing strong activation of the cytotoxic lymphocytes, complicate, however, the build-up of the particles and economical production thereof and are associated with an increased toxicity risk and physiological transport restrictions.

WO 2001/12221 A1 describes for silicon dioxide an intrinsic adjuvant effect in combination with proteinogenic antigens, cells or cell fragments, which is based on rough edges and an irregular shape, as a consequence of which the penetration of cell membranes and the modification of surface proteins is facilitated. By contrast, WO 2007/030901 A1 and Vallhov et al. (2007), Nano Lett. 7(12), 3576, associate the adjuvant effect with the mesoporosity of the silica particles. Irrespective of the underlying cause, EP 0 465 081 B1 has already taught a preparation comprising a core particle of metal, ceramic (for example silicon dioxide) or polymer, a coating, at least partly covering the surface of this core particle, which comprises a basic sugar, a modified sugar or an oligonucleotide, and at least one viral protein or peptide which is in contact with the coated core particle. The core particles have a diameter of 10 to 200 nm, but agglomerate to form larger particles, which is even desired, since a depot effect thus becomes established. It is disadvantageous that agglomerations of this type mean that it is neither possible to produce pharmaceutically stable suspensions nor to achieve sterile filterability.

The invention is based on the object of overcoming the disadvantages indicated in the prior art and developing nanoparticles which have a monodisperse particle size and enable effective application in immunoprophylaxis or immunotherapy, in particular as vaccines, which improve the therapeutic efficacy at the same time as reducing the side effects.

DESCRIPTION OF THE INVENTION

Figure 1:
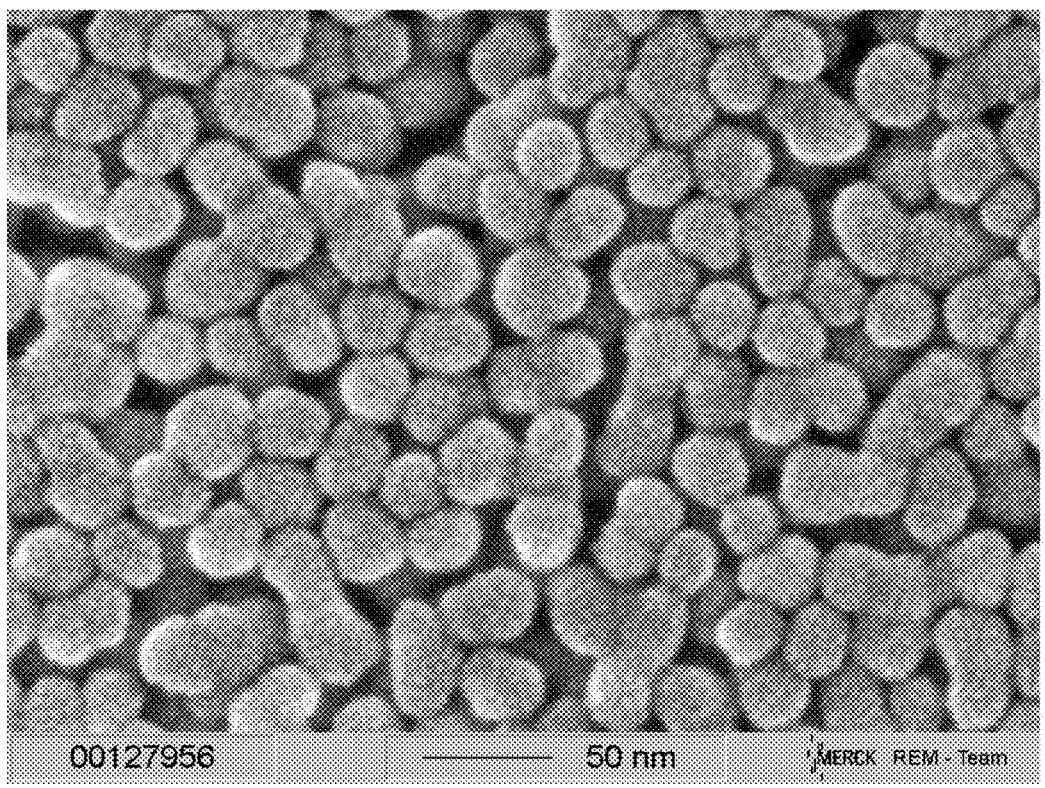
FIG. 1 depicts the particle size and morphology of the spherical silicon dioxide particles produced in Example 1, by means of an SEM photomicrograph.

The object of the invention is achieved in accordance with the independent claims. The sub-claims contain preferred embodiments. In accordance with the invention, nanoparticles are provided which comprise a matrix which comprises more than 50% of silicon dioxide, where the silicon dioxide has at least one surface functionality to which at least one antigen is attached, and where the nanoparticles have a size of 5 to 50 nm. The particle size here should be interpreted in such a way that a random distribution over the entire range between 5 and 50 nm is not present, but instead a defined particle size within the above-mentioned range is selected, of which the standard deviation is a maximum of 15%, preferably a maximum of 10%. In an embodiment of the present invention, the particles have a size between 10 and 30 nm, preferably between 20 and 30 nm, particularly preferably between 13 and 29 nm, very particularly preferably of 25 nm±10%.

Surprisingly, it has been found that the provision of silicon dioxide nanoparticles in a narrow size range between 5 and 50 nm can significantly increase the efficiency of antigen targeting at antigen-presenting cells. In particular, it is no longer peripheral dendritic cells that are primarily targeted, but instead the dendritic cells of the lymph nodes. The nanoparticles according to the invention are designed through their size and choice of materials in such a way that effective induction of the maturation of dendritic cells takes place. This induction occurs, in particular, via activation of the complement system. The silicon dioxide nanoparticles according to the invention thus open up completely new opportunities with respect to the targeting of lymph nodes having a high dendritic cell density and with respect to the pathway of dendritic cell maturation as a prerequisite for T-cell proliferation and immunisation. It is noteworthy that a vaccine based on these nanoparticles does not need the adjuvants which are otherwise unavoidable in vaccination.

To date, it is merely known from U.S. Pat. No. 6,086,881 that the vaccine material should have a high molecular weight which increases the probability of antigenic determinants. It is likewise desired for the vaccine material to aggregate or adsorb on alum or other gels since it usually becomes more effective with respect to cell binding and stimulation of cell surface molecules and the antigen is retained in the tissue over longer periods owing to the slow desorption rate. It is also confirmed by Vallhov et al. (2007), Nano Lett. 7(12), 3576, that larger particles comprising mesoporous silicon dioxide have a greater influence on human dendritic cells derived from monocytes. In addition, antigen-silica conjugates for targeting at antigen-presenting cells, for which a particle size of 0.3 to 20 μm is regarded as necessary prerequisite for phagocytosis, are described in the prior art in accordance with WO 2008/019366 A2. By contrast, the present invention reveals that specifically silicon dioxide nanoparticles in a defined narrow size range from 5 to 50 nm are capable of passive targeting at antigen-presenting cells and of complement activation.

An "antigen-presenting cell" in the sense of the invention is taken to mean any cell which can be induced to present antigens to a T-cell, which also includes precursor cells which can be differentiated and activated to antigen-presenting cells. Antigen-presenting cells include dendritic cells, Langerhans cells, PBMCs, macrophages, B lymphocytes or other activated or modified cell types, such as, for example, epithelial cells, fibroblasts and endothelial cells which express MHC molecules on their cell surfaces, preferably dendritic cells, particularly preferably dendritic cells of the lymph nodes. Precursors of antigen-presenting cells include $CD34^+$ cells, monocytes, fibroblasts and endothelial cells.

In accordance with the invention, the particulate binding matrix comprises more than 50% of silicon dioxide. The binding matrix may thus also be admixed with further components, where silicon dioxide exhibits the highest proportion in a multicomponent system. Examples of other components are metals, metal derivatives, metal oxides, polymers, organosilanes, other ceramics or glass. In an embodiment of the present invention, however, polymers are excluded as further components. It is preferred for the matrix to comprise at least 80% of silicon dioxide, particularly preferably at least 90%. In a very particularly preferred embodiment of the nanoparticles according to the invention, the matrix comprises silicon dioxide which is essentially pure, i.e. only comprises the impurities to be expected in the course of the preparation process. In an extremely preferred embodiment of the invention, the particulate binding matrix consists of silicon dioxide.

The particles can be prepared using, inter alia, the classical Stober synthesis, in which monodisperse nanoscale silicon dioxide of defined size can be prepared by hydrolysis of tetraethoxysilane (TEOS) in aqueous-alcoholic-ammoniacal medium (J. Colloid Interface Sci. 1968, 26, 62). Surprisingly, the inventors were able to show that the stability of the nanoparticles is retained in spite of surface functionalisation, as a consequence of which monodisperse particles which do not tend towards agglomeration are obtained. Preference is consequently given in accordance with the invention to nanoparticles produced by a process having the following steps:

(a) hydrolytic polycondensation of tetraalkoxysilanes and/or organotrialkoxysilanes in a medium which comprises water, at least one solubiliser and at least one amine or ammonia, where firstly a sol of primary particles is produced, and the resultant nanoparticles are subsequently brought to the desired particle size in a range from 5 to 50 nm in such a way that further nucleation is prevented by continuous metering-in of corresponding silane in a controlled manner corresponding to the extent of reaction, and
(b) attachment of an antigen to a surface functionality of the nanoparticles.

If ammonia is a constituent of the medium, the solubiliser used is, in particular, alcohol, so that the reaction proceeds in an aqueous-alcoholic-ammoniacal medium, giving highly monodisperse particles whose standard deviation from the average particle diameter is not greater than 10%. Surprisingly, the inventors have now found that the process even enables particle diameters below 50 nm to be achieved with the desired monodisperse properties. Step (a) of the process is described in detail in EP 0 216 278 B1 and WO 2005/085135 A1, and consequently these documents are incorporated in their totality into the disclosure content of the present invention by way of reference. At least one amine is preferably used in the medium.

The silicon dioxide matrix of the nanoparticles according to the invention can be either porous or non-porous. The porosity is essentially dependent on the production process. In the synthesis in accordance with EP 0 216 278 B1, non-porous particles, in particular, are obtained. Within the entry range from 5 to 50 nm, a preferred particle size for non-porous nanoparticles is between 10 and 30 nm, while the preferred particle size for porous particles is 10 to 40 nm. Preferred particles of the invention are solid.

In connection with the present invention, a "nanoparticle" is taken to mean a particulate binding matrix which has functionalities on its surface which function as recognition points for antigens ultimately to be bound or adsorbed. The surface here encompasses all areas, i.e. besides the outer surface, also the inner surface of cavities (pores) in the particle. In an embodiment according to the invention, the antigen can consequently be taken up into the particles, which requires porosity of the silicon dioxide matrix.

The surface functionality may consist of one or more chemical groups, which may in turn be identical or different, where the groups either enable specific attachment of nanoparticles and antigen in their property as linkers or form a non-specific zeta potential for attachment.

The term "attachment" here relates to any type of interaction between the surface functionality and the antigen, in particular covalent or non-covalent bonds, such as, for example, a covalent bond, hydrophobic/hydrophilic interactions, van der Waals forces, ionic bonding, hydrogen bonds, ligand-receptor interactions, base pairing of nucleotides or interactions between epitope and antibody binding site.

In a preferred embodiment of the present invention, the antigen is covalently bonded to the nanoparticle. The covalent bonding can take place either directly or indirectly. In the direct variant, the antigen is conjugated directly onto a chemical group on the particle, which usually takes place non-site-specifically and may make later liberation in the phagosome of the antigen-presenting cell more difficult. In an embodiment of the invention, it is desired for thioethers, carbohydrates and/or oligonucleotides to be excluded as surface functionality. The indirect method of covalent linking uses a linker or tag via which the antigen is bonded site-specifically to the particles and is liberated again in a controlled manner. Tags for site-specific conjugation are known from the prior art, such as, for example, SNAP tag, halo tag, C-terminal LPXTG tag, biotin acceptor peptide, PCP or ybbR tag, and are described, inter alia, in WO 2008/019366 A2, and consequently this document is incorporated in its totality into the disclosure content of the present invention by way of reference. This reference also applies with respect to all further mentions of this document in the course of the present specification.

In a preferred embodiment of the surface functionality, it is represented by a labile linker, particularly preferably by a hydrazone linker, disulfide linker or a peptide sequence which is readily accessible enzymatically. In a first clinical candidate, doxorubicin is bonded to the polymer via an acid-labile hydrazone bond as nominal breaking point (Angew. Chem. 2006, 118, 1218). The macromolecules are taken up into the cell by endocytosis, while a significant drop in the pH from the physiological value in the extracellular space (pH 7.2-7.4) to pH 6.5-6 in the endosome and to pH 4 in primary and secondary lysosomes occurs. If the pH drops below 6 as a consequence of cellular uptake, the hydrazone link breaks and the active compound is released by the polymeric support. Further cleavable linkers which are suitable for the purposes of the invention and are described in the further course of the specification are known to the person skilled in the art.

In a further preferred embodiment of the surface functionality, it is selected from the group of the alkoxysilanes. It is particularly preferred here for it to be a terminal, reactive thiol group. Alkoxysilanes can be employed both for attachment of the antigen and also of further ligands of other functions, where the attachment of the latter by means of this stable linker is preferred. Suitable alkoxysilanes for the purposes of the nanoparticles according to the invention can be selected routinely by the person skilled in the art.

In another embodiment of the present invention, the antigen is adsorbed on the nanoparticle. The adsorption can be carried out, for example, by mixing the antigen with the particles within a defined time span, after which the nanoparticles are separated off from the mixture, such as, for example, by means of centrifugation or filtration. The charging can even take place during the particle synthesis. It goes without saying for the purposes of the invention that the adsorption also requires a suitable surface functionality (zeta potential), which can either be an inherent constituent of the matrix or has to be introduced in another manner.

If the surface does not already carry a functionalisation, depending on the synthetic route selected, this is introduced before attachment of the antigen. If the nanoparticles are produced by hydrolytic polycondensation in accordance with process step (a) mentioned above, the functionalisation of the surface is carried out after step (a) and before step (b). Many of the silicon atoms on the particle shell carry hydroxyl functions, which are able to react with a multiplicity of commercially available trialkoxysilanes or trichlorosilanes by standard methods, meaning that the particles can be functionalised in various ways in a simple manner (J. Liq. Chrom. & rel. Technol. 1996, 19, 2723). If the target applications or the desired properties of the nanoscale silicon dioxide particles require greater chemical complexity, well-thought-out multistep syntheses are used.

Finally, the antigen is attached to the nanoparticle by interaction with the surface functionality.

An "antigen" here is taken to mean a structure which is capable of generating a cellular or animal immune response. It goes without saying that the immune response in an animal includes all mammals, in particular humans. Antigens are preferably proteinogenic, i.e. they are proteins, polypeptides, peptides or fragments thereof, which may in turn be of any desired size, origin and molecular weight and may be glycosylated, but contain at least one antigenic determinant or an antigenic epitope. Recognition by the immune system takes place, in particular, from a minimum length of three amino acids. The proteins or peptides are preferably selected from the group of the cytokines, receptors, lectins, avidins, lipoproteins, glycoproteins, oligopeptides, peptide ligands and peptide hormones. Antigens may also be nucleic acids per se or encoded by nucleic acids, which, after transport into the core of antigen-presenting cells, are translated into the proteinogenic antigen which is presented to MHC molecules. The nucleic acids are single- and double-stranded DNA or RNA and oligonucleotides. The nucleic acids may also be a constituent of complexes or formulations which consist of lipids, carbohydrates, proteins or peptides. Further antigens are polysaccharides, polymers, low-molecular-weight substances having a molecular weight of 50 to 1000 Da, viruses, intact prokaryotic or eukaryotic cells or cellular fragments.

In an embodiment of the invention, the antigen has a molecular weight of less than 500 kDa. The antigen is preferably a cancer antigen. Cancer antigens of this type are disclosed, for example, in WO 2008/019366 A2. In a particularly preferred embodiment, the cancer antigen is selected from the group comprising New York oesophageal 1 antigen (NY-ESO-I), MAGE-A1, MAGE-A2, MAGE-A3, MAGE-A4, MAGE-A6, MAGE-A8, MAGE-A10, MAGE-B, MAGE-C1, MAGE-C2, L antigen (LAGE), SSX2, SSX4, SSX5, PRAME, melan-A, caspase-8, tyrosinase, MAGF, PSA, CEA, HER2/neu, MUC-1, MART1, BCR-abl, p53, ras, myc, RB-1 and survivin or epitopes thereof. In a very particularly preferred embodiment of the invention, the cancer antigen is survivin or epitopes thereof. This cancer antigen is described in WO 2007/039192 A2, and consequently this document is incorporated in its totality into the disclosure content of the present invention by way of reference.

In another embodiment of the invention, receptors and/or MHC molecules are excluded both as surface functionality and antigen.

The nanoparticles may be multifunctionalised, which, in the sense of the invention, means different chemical groups (surface functionalities) and/or different bonded molecules (functions). It is preferred for both the surface functionalities and the bonded functions to be different, giving rise to specific, independent bonding of the functional molecules. The functions are preferably selected from the group of antigen, polyethylene glycol (PEG), labelling and adjuvant, where it goes without saying that the antigen is always selected. Antigen and PEG and/or adjuvant are particularly preferably present, very particularly preferably antigen, PEG and adjuvant, where these functions may be bonded adsorptively and/or covalently.

In an embodiment of the particles according to the invention, the labelling is detected by luminescence, UV/VIS colouring, enzymatically, electrochemically or radioactively. Fluorescent dyes or radioactive labels are preferably used. In the case of photoluminescence or fluorescence, the excitation is carried out by absorption of photons. Preferred fluorophores are bisbenzimidazoles, fluorescein, Acridine Orange, Cy5, Cy3 or propidium iodide. The evaluation is carried out visually or using appropriate measuring instruments, for example under a fluorescence microscope, or by flow cytometry, for example in a cytofluorimeter. In a particularly preferred embodiment of the invention, the fluorescent dyes are bonded to 3-aminopropyltriethoxysilane, where fluorescein isothiocyanate is a very particularly preferred fluorescent dye.

Alternatively, the detection can also be carried out radioactively using radioactive isotopes, preferably using 3H, 14C, 32P, 33P, 35S, 99mTc, 111In or 125I, particularly preferably using 99mTc or 111In. In particular, derivatives of 1,4,7,10-tetraazacyclododecane-N,N',N'',N'''-tetraacetic acid (DOTA) or diethylenetriaminepentaacetic acid (DTPA), which are bonded to the nanoparticles via click chemistry, are provided with the particularly preferred radioisotopes immediately before injection. In the case of scintillation counting, a molecule cocktail is, for example, excited by radioactive γ radiation. The energy liberated as light on transition into the ground state is amplified by a photoelectron multiplier and counted.

The nanoparticles according to the invention are thus also important as a diagnostic tool (for example in imaging methods) and/or research tool, which enables the visualisation of the targeting and active-compound uptake.

In a further embodiment of the invention, an antigen is combined with a label in such a way that assignment to the antigen can be carried out within a particle fraction via the label. This means that a first particle or a plurality thereof is provided with a first antigen and a first label, while a second particle or a plurality thereof is provided with a second antigen and a second label, etc., where both the antigens and the labels are in each case different from one another. The specific combination of antigen and label is consequently unique and preferred herein and enables mixing of particles with different antigens and the parallel monitoring of the targeting efficiency and/or immune/complement activation. This results in a saving of time in diagnostics compared with sequential administration. It is of course likewise possible for the particles to carry a plurality of antigens and a plurality of labels whose intensities vary, meaning that a certain antigen can be selected from the mixture. The label is preferably a fluorescent dye, which is bonded, in particular, to silane.

The nanoparticles of the invention may furthermore be designed as combinations of antigens and danger signals, such as, for example, TLRs or cytokines.

In yet a further embodiment of the present invention, the surface is multifunctionalised in such a way that crosslinking of the multifunctionalities is excluded.

The above teaching of the invention and embodiments thereof relating to the surface functionality for the attachment of antigens to nanoparticles are valid for and applicable without restrictions to multifunctionalities and/or the attachment of further functions to nanoparticles, so long as it appears appropriate.

A universal strategy for the construction of highly complex systems is the concept of click chemistry presented by K. B. Sharpless (Angew. Chem. Int. Ed. 2001, 40, 2004). This is more of a synthesis philosophy than a scientific discipline, which is inspired, in particular, by the simplicity and efficiency of naturally occurring reactions. A prime example of click chemistry has proven to be the 1,3-dipolar cycloaddition of azides and terminal alkynes by the Huisgen method. In the presence of monovalent copper, these reactions take place with drastic acceleration, and in addition proceed regioselectively, in very high yields and with tolerance of a wide range of functional groups. A further advantage lies in the possibility of carrying out the synthesis in an aqueous medium and at room temperature, enabling interesting biomolecules to be linked in a modular and widely applicable manner to other building blocks in a type of construction set principle. It is therefore preferred for the purposes of the invention to link the correspondingly functionalised silicon dioxide particles to the above-mentioned functions, in particular the antigens, using click chemistry.

The invention also relates to a dispersion which comprises the nanoparticles according to the invention. The nanoparticles can be in dispersed form in any desired solvent, so long as the nanoparticles are neither chemically attacked nor physically modified by the solvent, and vice versa, so that the resultant nanodispersion is stable, in particular pharmaceutically and physically stable. The dispersion is specifically characterised in that the nanoparticles are in monodisperse and non-aggregated form and have no tendency towards sedimentation, which results in sterile filterability. The above teaching of the invention and embodiments thereof relating to the nanoparticles are valid for and applicable without restrictions to the dispersions, so long as it appears appropriate.

The invention can also be practised as a kit which comprises the nanoparticles according to the invention and/or dispersions thereof. The kit of the invention may also contain an article which contains written instructions or points out to the user written instructions which explain the handling of the nanoparticles of the invention. The above teaching of the invention and embodiments thereof relating to the nanoparticles and dispersions thereof are valid for and applicable without restrictions to the kit, so long as it appears appropriate.

The invention also relates to a pharmaceutical composition which comprises the nanoparticles according to the invention or dispersions thereof. A "pharmaceutical composition" here is any composition which can be employed in the prophylaxis, therapy, control or post-treatment of patients who exhibit, at least temporarily, a pathogenic modification of the overall condition or the condition of individual parts of the patient organism, in particular as a consequence of infectious diseases, septic shock, tumours, cancer, autoimmune diseases, allergies and chronic or acute inflammation processes. Thus, in particular, it is possible for the pharmaceutical composition in the sense of the invention to be a vaccine and/or an immunotherapeutic agent. The pharmaceutical composition may comprise the antigens, such as, for example, peptides or nucleic acids, for example, as a pharmaceutically acceptable salt. This may be, inter alia, salts of inorganic acids, such as, for example, of phosphoric acid, or salts of organic acids.

In order to support the medical effect, i.e., in particular, the immune response, the pharmaceutical composition may, in an embodiment of the invention, also comprise further active compounds, where simultaneous or successive administration is conceivable. The therapeutic effect of the pharmaceutical composition according to the invention can arise, for example, through certain antitumour medicaments having a better action through activation of the complement system as a desired side effect or through the number of side effects of these medicaments being reduced by the reduction in the dose.

In a preferred embodiment of the invention, the pharmaceutical composition according to the invention is combined with chemotherapeutic agents, which are selected from the group comprising cytokines, chemokines, pro-apoptotic agents, interferons, radioactive compounds or combinations thereof. It is preferred for the chemotherapeutic agent to modify, in particular reduce, nucleic acid and/or protein metabolism, cell division, DNA replication, purine, pyrimidine and/or amino acid biosynthesis, gene expression, mRNA processing, protein synthesis, apoptosis or combinations thereof.

In order to stimulate the endogenous defences or to strengthen the immune system, it is also possible, in a further embodiment of the invention, to administer immunostimulants, for example interferons, such as, for example, IFN-$\alpha$, IFN-$\beta$ or IFN-$\gamma$, interleukins, such as, for example, IL-1, IL-2, IL-3, IL-4, IL-5, IL-6, IL-7, IL-8, IL-9, IL-10 or IL-12, tumour necrosis factors, such as, for example, TNF-$\alpha$ or TNF-$\beta$, erythropoietin, M-CSF, G-CSF, GM-CSF, CD2 or ICAM, with the present pharmaceutical composition. In this way, the proliferation, development, differentiation or activation of, for example, T lymphocytes, B lymphocytes, monocytes, macrophages, neutrophilic cells, eosinophilic cells, megakaryocytes and/or granulocytes can be stimulated.

In order to increase the protective or therapeutic action of the immunogenic nanoparticles according to the invention, pharmaceutically tolerated adjuvants can be added to the particles or all pharmaceutical compositions prepared therefrom. For the purposes of the invention, any substance which facilitates, enhances or modifies an effect with the antigens in accordance with the invention is an "adjuvant". Known adjuvants are, for example, aluminium compounds, such as, for example, aluminium hydroxide or aluminium phosphate, saponins, such as, for example, QS 21, muramyl dipeptide or muramyl tripeptide, proteins, such as, for example, gamma-interferon or TNF, MF 59, phosphatdibylcholine, squalene or polyols. The co-application of egg albumin in complete Freund's adjuvant can likewise cause an increased cell-mediated immunity and thus support the action of neutralising antibodies formed. Furthermore, DNA, which has an immunostimulatory property, or which encodes a protein with an adjuvant effect, such as, for example, a cytokine, can be applied in parallel or in a construct. Owing to the intrinsic adjuvant effect of the silicon dioxide-based nanoparticles according to the invention, however, it is preferred in the present case to use no further adjuvants. If the intrinsic adjuvant effect proves inadequate in certain applications, it is of course possible additionally to attach one or more adjuvants to the nanoparticles, preferably only one adjuvant. The type of attachment may either be adsorptive or consist of a covalent bond. Preferred adjuvants of the invention to be bonded adsorptively include poloxamers and TLRs. Preferred covalently bonded adjuvants of the invention include short-chain peptides, particularly preferably tuftsin or ovalbumin.

The introduction of the pharmaceutical composition into a cell or organism can be carried out in accordance with the invention in any manner which enables the antigen-presenting cells to be brought into contact with the nanoparticles or antigens present in the composition and taken up into the cells by phagocytosis, as a consequence of which an immune response is induced. The pharmaceutical composition of the present invention can be administered orally, transdermally, transmucosally, transurethrally, vaginally, rectally, pulmonarally, enterally and/or parenterally. Parenteral administration of the pharmaceutical composition is preferred. It has been shown in the present case that silicon dioxide in its property as adjuvant has no adverse effects on the lipid balance, as observed for polymeric adjuvants, which are consequently not approved for this type of application. Direct injection into the body is particularly preferred. The type of administration selected depends on the indication, the dose to be administered, individual-specific parameters, etc. In particular, the various types of administration facilitate site-specific therapy, which minimises side effects and reduces the active-compound dose. Very particularly preferred injections are intradermal, subcutaneous, intramuscular or intravenous injection. The administration can be carried out, for example, with the aid of so-called vaccination guns or by means of syringes. It is also possible to prepare the substance as an aerosol, which is inhaled by the organism, preferably a human patient.

The administration forms of the pharmaceutical composition are prepared corresponding to the desired type of administration in a suitable dosage and in a manner known per se using the conventional solid or liquid vehicles and/or diluents and the assistants usually employed. Thus, pharmaceutically acceptable excipients known to the person skilled in the art can basically form part of the pharmaceutical composition according to the invention, where the amount of excipient material which is combined with the active compound in order to prepare a single dose varies depending on the individual to be treated and the type of administration. These pharmaceutically tolerated additives include salts, buffers, fillers, stabilisers, complexing agents, antioxidants, solvents, binders, lubricants, tablet coatings, flavours, dyes, preservatives, adjusters and the like. Examples of excipients of this type are water, vegetable oils, benzyl alcohols, alkylene glycol, polyethylene glycol, glycerol triacetate, gelatine, carbohydrates, such as, for example, lactose or starch, magnesium stearate, talc and Vaseline.

The pharmaceutical formulation can be in the form of a tablet, film tablet, dragee, lozenge, capsule, pill, powder, granules, syrup, juice, drops, solution, dispersion, suspension, suppository, emulsion, implant, cream, gel, ointment, paste, lotion, serum, oil, spray, aerosol, adhesive, plaster or bandage, where the dispersion is preferred.

Oral administration forms which are prepared are preferably tablets, film tablets, dragees, lozenges, capsules, pills, powders, granules, syrups, juices, drops, solutions, dispersions or suspensions—including as depot form. Medicament forms as tablets can be obtained, for example, by mixing the active compound with known assistants, such as dextrose, sugar, sorbitol, mannitol, polyvinylpyrrolidone, disintegrants, such as maize starch or alginic acid, binders, such as starch or gelatine, lubricants, such as magnesium stearate or talc, and/or agents which are able to achieve a depot effect, such as carboxypolymethylene, carboxymethylcellulose, cellulose acetate phthalate or polyvinyl acetate. The tablets may also consist of a plurality of layers. Dragees can likewise be prepared by coating cores produced analogously to the tablets with agents usually used in dragee coatings, for example polyvinylpyrrolidone or shellac, gum arabic, talc, titanium dioxide or sugar. The dragee shell here may also consist of a plurality of layers, where, for example, the above-mentioned assistants are used. The capsules can be produced by mixing the active compound with vehicles, such as lactose or sorbitol, which are then introduced into capsules. The solutions or dispersions of the pharmaceutical composition can be mixed with substances, such as, for example, saccharin, cyclamate or sugar types, and/or with aromas, such as, for example, vanillin or orange extract, in order to improve the taste. Furthermore, they can be mixed with suspension assistants, such as, for example, sodium carboxymethylcellulose, or preservatives, such as, for example, p-hydroxybenzoic acid, phenol, benzyl alcohol, m-cresol, methylparaben, propylparaben, benzalkonium chloride or benzethonium chloride.

Furthermore, parenteral medicament forms, such as, for example, suppositories, suspensions, emulsions, implants or solutions, should be considered, preferably oily or aqueous solutions. For parenteral administration, the immunogenic construct of the invention can be dissolved or suspended in a physiologically tolerated diluent, such as, for example, neutral fats or polyethylene glycols or derivatives thereof. The preferred solvents used are frequently oils, with or without addition of a solubiliser, a surface-active agent, a suspension agent or emulsifier. Examples of oils used are olive oil, peanut oil, cottonseed oil, castor oil and sesame oil.

For topical application of the pharmaceutical composition, the latter is formulated in a conventional manner with at least one pharmaceutically acceptable vehicle, such as, for example, microcrystalline cellulose, and optionally further assistants, such as, for example, moisturisers, to give solid formulations which can be applied to the skin, such as, for example, creams, gels, ointments, pastes, powders or emulsions, or to give liquid formulations which can be applied to the skin, such as, for example, solutions, suspensions, lotions, sera, oils, sprays or aerosols. Examples are solutions in alcohols, such as, for example, ethanol or isopropanol, acetonitrile, DMF, dimethylacetamide, 1,2-propanediol or mixtures thereof with one another and/or with water. Liposomes, which guarantee optimum transport into the skin, can also serve as carrier systems for the pharmaceutical composition. Suitable topical preparations are also transdermal systems, such as, for example, solutions, suspensions, creams, ointments, powders, gels, emulsions, adhesives, plasters or bandages, which comprise the nanoparticles together with a vehicle. Useful vehicles may comprise absorbable, pharmacologically suitable solvents in order to support passage of the nanoparticles through the skin. Solvents which guarantee good penetration into the skin are, for example, the alcohols phenyl-1-ethanol, glycerol, ethanol or mixtures thereof.

The pharmaceutical composition is preferably in the form of an injection solution. For the preparation of the injection solution, aqueous media, such as, for example, distilled water or physiological salt solutions, can be used, where the latter include acidic and basic addition salts. The pharmaceutical composition may also be in the form of a solid composition, for example in the lyophilised state, and can then be prepared before use by addition of a dissolving agent, such as, for example, distilled water. The person skilled in the art is familiar with the basic principles of the preparation of lyophilisates.

The concentration of the active nanoparticles in the formulation can vary between 0.1 to 100 percent by weight. It is crucial that the pharmaceutical composition comprises, as active compound, an effective amount of the nanoparticles and/or dispersion thereof together with the pharmaceutically tolerated assistants. The terms "effective amount" or "effective dose" are used interchangeably herein and denote an amount of the pharmaceutical active compound which has a prophylactically or therapeutically relevant action on a disease or pathological change. A "prophylactic action" prevents the outbreak of a disease or even infection with a pathogen after ingress of individual representatives in such a way that subsequent spread thereof is greatly reduced or they are even completely deactivated. A "therapeutically relevant action" frees from one or more disease symptoms or results in the partial or complete reversal of one or more physiological or biochemical parameters which are associated with or causally involved in the disease or pathological change, into the normal state. The respective dose or dose range for the administration of the nanoparticles according to the invention is sufficiently large to achieve the desired prophylactic or therapeutic effect of induction of an immune response. In general, the dose will vary with the age, constitution and gender of the patient, and the severity of the disease will be taken into account. It goes without saying that the specific dose, frequency and duration of administration are, in addition, dependent on a multiplicity of factors, such as, for example, the targeting and binding ability of the nanoparticles, nutrition habits of the individual to be treated, type of administration, excretion rate and combination with other medicaments. The individual dose can be adjusted both with respect to the primary disease and also with respect to the occurrence of any complications. The precise dose can be established by a person skilled in the art using known means and methods. This teaching of the invention is valid for and applicable without restrictions to the pharmaceutical composition comprising the nanoparticles and/or dispersions thereof, so long as it appears appropriate.

In an embodiment of the invention, the nanoparticles are administered in a dose of 0.01 mg to 1 g per kilogram of body weight and per day. However, doses of 20 to 60 mg per kilogram of body weight and per day are preferably administered. The daily dose is preferably between 0.02 and 10 mg/kg of body weight.

In accordance with the invention, the present nanoparticles and/or nanoparticle dispersions are suitable for the prophylactic or therapeutic treatment of diseases which are selected from the group of infectious diseases, septic shock, tumours, cancer, autoimmune diseases, allergies and chronic or acute inflammation processes. It goes without saying that the host of the pharmaceutical composition is also included in the scope of protection of the present invention.

In a preferred embodiment, the cancer or tumour disease which is treated, prophylactically prevented or whose recurrence is prevented is selected from the group of cancer or tumour diseases of the ear-nose-throat region, mediastinal cavity, gastrointestinal tract (including: colon carcinomas, stomach carcinomas, colonic cancer, cancer of the small bowel, pancreatic carcinomas, liver carcinomas), urogenital system (including kidney cell carcinomas), gynaecological system (including ovarian carcinomas) and endocrine system and of the lung (including lung cancer), breast (including breast carcinomas) and skin, and bone and soft-part sarcomas, mesotheliomas, melanomas, neoplasms of the central nervous system, paediatric cancer diseases or tumour diseases, lymphomas, leukaemias, paraneoplastic syndromes, metastases without known primary tumour (CUP syndrome), peritoneal carcinomatoses, immunosuppression-related malignancies, multiple myelomas and tumour metastases.

The autoimmune diseases to which the invention relates are preferably selected from the group comprising arthritis, autoimmune hepatitis, chronic gastritis, neurodermatitis, psoriasis, arthrosis, rheumatic diseases, rheumatoid arthritis, juvenile idiopathic arthritis, Crohn's disease, suppurative inflammation of the colon, diabetes, inflammatory bowel diseases, multiple sclerosis and/or allergic inflammations.

In accordance with the invention, the nanoparticles are also employed for the prophylaxis or therapy of diseases which are caused by microorganisms which may be pathogenic to mammals. This means that the action according to the invention is directed either against microorganisms which are able to carry out health-damaging processes to their own advantage through a disturbance in the natural equilibrium of the microorganism flora which colonises a host organism and/or in the case of hosts which have a weakened immune system, or against those which are inherently pathogenic. Preferred microorganisms in the sense of the invention are viruses, bacteria, fungi and/or singlecelled animals. Particular preference is given to bacteria, where Gram-positive and Gram-negative bacteria are influenced in their growth. Examples of diseases which can be treated with the nanoparticles are hepatitis B, hepatitis C, HIV, herpes, tuberculosis, leprosy or malaria, which are caused by the above-mentioned microorganisms.

It is known to the person skilled in the art that the induction of T-cell proliferation and/or neutralising antibodies may be advantageous at virtually any time. In the present case, the nanoparticles and dispersions thereof are employed primarily for immunotherapy, meaning that vaccination in the sense of the invention is preferably an administration of the pharmaceutical composition according to the invention after diagnosis and/or outbreak of a disease which responds to immunotherapy. The vaccination should preferably be carried out a short time after diagnosis or outbreak of the disease and can also be administered a number of times as therapy in order to enhance the initial proliferative immune response of the organism by a number of injections. Consequently, monitoring is also taken to mean a type of therapeutic treatment if the nanoparticles are administered at certain intervals, for example in order completely to eliminate the symptoms of a disease. In a preferred embodiment of the present invention, the nanoparticles and/or dispersions thereof are used for the therapy of cancer and/or tumours, particularly preferably for cancer therapy.

It is of course likewise advantageously possible for active vaccination protection to develop after prophylactic administration in the organism. Prophylactic immunotherapy is advisable, in particular, if an individual is predisposed to the outbreak of the above-mentioned diseases, such as, for example, a family history, a gene defect or a recently survived disease.

The invention thus also relates to the use of the nanoparticles according to the invention and/or the dispersion according to the invention for immunoprophylaxis or immunotherapy. The invention furthermore relates to the use of an effective amount of the nanoparticles according to the invention and/or the dispersion according to the invention for the preparation of a vaccine for immunoprophylaxis or immunotherapy. In both subject-matters, the diseases to be treated are selected from the group which includes infectious diseases, septic shock, tumours, cancer, autoimmune diseases, allergies and chronic or acute inflammation processes. The vaccine is prepared, in particular, by non-chemical methods by converting the active compound into a suitable dosage form together with at least one solid, liquid and/or semi-liquid vehicle or assistant and optionally in combination with one or more further active compounds. The above teaching of the invention and embodiments thereof are valid for and applicable without restrictions to the nanoparticles, dispersions and the medical use thereof, so long as it appears appropriate.

A further embodiment of the invention relates to the use of the nanoparticles according to the invention and/or dispersions thereof for the targeting of antigens at antigen-presenting cells and optionally for the activation of the immune system, preferably for the activation of the complement system. The targeting is preferably carried out ex vivo or in vitro by administering the antigen-carrying nanoparticles to cells, cell cultures, tissues or organs which comprise antigen-presenting cells. The ex vivo use is used, in particular, in the case of animal cells which originate from an animal organism which is affected by a disease selected from the group of infectious diseases, septic shock, tumours, cancer, autoimmune diseases, allergies and chronic or acute inflammation processes. The ex vivo-treated cells can either continue to be kept in culture for subsequent investigations or can be transferred into an animal, which may be the host animal or another animal. The ex vivo targeting according to the invention is advantageous, in particular, in order to test the specific structure of the nanoparticles with respect to particle size, antigen, attachment and multifunctionalisation, enabling the in vivo dose to be set correspondingly in advance on evaluation of these ex vivo data. As a result, the therapeutic effect in the form of the acquired immune response is significantly increased. It is likewise possible to stimulate the T-cells of a patient outside the body directly by means of the antigen-presenting cells which were exposed to the nanoparticles and then either to implant the T-cells or to use the T-cells for research purposes.

In a preferred embodiment of the use according to the invention, the antigens are directed to dendritic cells. In a particularly preferred embodiment of this use, the dendritic cells are located in lymph nodes. It goes without saying that the last-mentioned embodiment requires at least one tissue or organ, but in the best case an intact animal organism. It likewise goes without saying that this prerequisite must be met for immune or especially complement activation.

The nanoparticles can accordingly be used in vivo by administering them directly to an animal, in particular a mammal, particularly preferably a human, via known routes. The nanoparticles can furthermore be employed ex vivo, where the antigen-presenting cells are firstly isolated from an animal and subsequently treated ex vivo with the nanoparticles according to the invention in such a way that the nanoparticles are taken up by the cells. The antigen-presenting cells treated in this way are returned to the body, as a consequence of which the T-cells of the organism are stimulated.

Consequently, the invention furthermore relates to a method for the targeting of antigens at antigen-presenting cells having the following steps:
 (a) provision of nanoparticles essentially comprising pure silicon dioxide which has a surface functionality to which at least one antigen is attached, (b) administration of the nanoparticles to antigen-presenting cells present in cell culture, tissue, organs or an animal, (c) targeting of the antigens at antigen-presenting cells via the interstitial fluid by adjusting the targeting efficiency via the size of the nanoparticles, which are at least partially inversely proportional.

In step (a) of the method according to the invention, the nanoparticles are preferably provided by the following steps:

(a') hydrolytic polycondensation of tetraalkoxysilanes and/or organotrialkoxysilanes in a medium which comprises water, at least one solubiliser and at least one amine or ammonia, where firstly a sol of primary particles is produced, and the resultant nanoparticles are subsequently brought to the desired particle size in such a way that further nucleation is prevented by continuous metering-in of corresponding silane in a controlled manner corresponding to the extent of reaction, (a'') attachment of at least one antigen to a surface functionality of the nanoparticles, and optionally (a''') dispersal of the nanoparticles.

In step (b) of the method according to the invention, the nanoparticles are preferably administered to an animal, particularly preferably a mammal, very particularly preferably a human. The administration is carried out, in particular, parenterally, particularly preferably intradermally or subcutaneously.

In step (c), it has been found, unexpectedly, that the targeting of silicon dioxide particles can be influenced via the size of the nanoparticles. Whereas a particle size of about 150 nm represents the upper limit at which targeting is still observed, the efficiency of the targeting is increased at a smaller particle size. The size range of the particles is preferably greater than 0 nm and smaller than 150 nm, particularly preferably between 5 and 50 nm, very particularly preferably between 10 and 30 nm, most preferably between 13 and 29 nm.

In an embodiment of the invention, the targeting efficiency and the size of the nanoparticles are inversely proportional throughout the range. The efficiency can be increased either in a linear manner or in a non-linear manner, preferably in a non-linear manner.

In another embodiment of the invention, it is possible for the inverse proportionality between targeting efficiency and particle size not to exist throughout the size range, but instead for the correlation according to the invention to approach a maximum value for the targeting efficiency which is not observed at the smallest particle size and thus the end point of the size range. In this embodiment of the method according to the invention, the dependence of the targeting efficiency (on the ordinate) on the particle size (on the abscissa) is preferably described by an exponential function with natural, even exponents greater than/equal to 2, whose parabola is open at the bottom, so that the vertex represents the maximum efficiency. A quadratic function is particularly preferred. In other words, this means that the inverse proportionality is observed to a vertex (inflection point) in the above-mentioned particle-size range between 0 and 150 nm.

By means of the method, partial targeting can be set specifically or maximisation of the targeting can be achieved. In an embodiment of the present method, more than 50%, preferably more than 70%, particularly preferably more than 85%, very particularly preferably more than 95%, of the antigen-presenting cells in lymph nodes are targeted. For this purpose, it is in turn preferred to employ nanoparticles having a size of 5 to 50 nm. The particle size includes at least the silicon dioxide matrix, preferably the entire nanoparticle.

In a further embodiment of the method according to the invention, step (c) is followed by further steps:

(d) uptake of the nanoparticles into the antigen-presenting cells, and optionally (e) liberation of the antigens in the endosome.

It is preferred for both steps (d) and (e) to be carried out after step (c). The kinetics of antigen liberation by the particulate binding matrix after endocytosis can be controlled in step (e) by the antigens being covalently bonded to the vehicle via a so-called cleavable linker. For example, a pH-sensitive bond, an enzymatic interface (for example protease-sensitive linker) and/or a reductively or oxidatively cleavable linker can be incorporated as surface functionality. Preferred pH-sensitive bonds of the invention are achieved by certain esters, disulfide bridges, a hydrazone linker, an anhydride bond, self-cleaving intein sequences, pH-sensitive complexing agents or polymers, such as, for example, polyethylene oxide-modified poly-β-amino esters. The covalent bonding of the antigens via a labile linker as surface functionality is essential for step (e), where a hydrazone linker, a disulfide linker or a peptide sequence which is readily accessible enzymatically are preferred. It is furthermore preferred for the antigens to be liberated in the early endosome.

The above teaching of the invention and embodiments thereof relating to the nanoparticles, dispersions thereof, pharmaceutical compositions and use are valid for and applicable without restrictions to the method for targeting antigens at antigen-presenting cells, so long as it appears appropriate.

The invention furthermore relates to a method for the activation of the immune system in a mammal, in which, in a first step (a), nanoparticles are steered to antigen-presenting cells in accordance with the method according to the invention described above, and, in a second step (b), the immune system is activated. The complement system is preferably activated. In step (b), the activation efficiency can be adjusted via the particle characteristics, which include, in particular, particle size, surface functionality, surface charging and type, ratio, amount and density of the ligands (for example antigen, PEG, adjuvant). It is preferred in step (b) to adjust the activation efficiency via the particle size, which are at least partially inversely proportional. The activation efficiency increases, in particular, with smaller particle size. The above teaching of the invention and embodiments thereof relating to the method for targeting antigens at antigen-presenting cells is valid for and applicable without restrictions to the method for the activation of the immune or complement system in a mammal, so long as it appears appropriate.

The invention furthermore teaches a vaccination method, in which an effective amount of the nanoparticles according to the invention and/or dispersions comprising these nanoparticles is administered to a mammal which is in need of such a treatment. The mammal to be treated is preferably a human. The above teaching of the invention and embodiments thereof are valid for and applicable without restrictions to the treatment method, so long as it appears appropriate.

The invention furthermore teaches a method for the induction of a T-cell response, antibody response and/or dendritic cell maturation, characterised in that the nanoparticles according to the invention, which may be in the form of a dispersion and/or pharmaceutical composition, are administered to a mammal, and the proliferation of T-cells and/or dendritic cells and/or the formation of neutralising antibodies are induced. Preferred organisms in the sense of the invention are humans or animals. The disclosure of the nanoparticles according to the invention enables the person skilled in the art to use these for the induction of T-cells and/or neutralising antibodies.

It is known to the person skilled in the art here that he is able to administer the nanoparticles according to the invention, which can of course also be used as pharmaceutical composition according to the invention, in various dosages to an organism, in particular a human patient. The administration here should be carried out in such a way that the largest possible amount of T-cells and/or neutralising antibodies is generated. The concentration and type of administration can be determined by the person skilled in the art by routine experiments.

The bringing into contact of the nanoparticles or pharmaceutical composition can be carried out prophylactically or therapeutically. In the case of, for example, prophylactic vaccination for the development of active vaccination protection against viral infectious diseases, the infection with the viruses should at least be prevented in such a way that, after ingress of individual viruses, for example into a wound, further multiplication thereof is greatly reduced or that viruses that have ingressed are killed off virtually completely. In the case of therapeutic induction of an immune response, an infection of the patient already exists, and the induction of the T-cells and/or neutralising antibodies is carried out in order to kill off the viruses already present in the body or to inhibit their multiplication.

The invention furthermore relates to a method for the passive immunisation of an organism, characterised in that the T-cells and/or antibodies which have been induced by the administration of the nanoparticles according to the invention with a mammal are isolated and administered to a further mammal. A "further mammal" in the sense of the invention is taken to mean both organisms of the same species or of different species, but not the same organism which has induced the said T-cells and/or antibodies. It is also possible to isolate monoclonal antibodies, which are employed, inter alia, after corresponding humanisation. Antibody-producing cells can likewise be isolated from vaccinated or infected individuals who produce neutralising antibodies which are directed against the nanoparticles according to the invention, and are administered in the form of monoclonal antibodies in the case of passive immunisation.

In passive immunisation, essentially no inherent immune reaction to, for example, certain viruses takes place in the body of the patient, but instead the T-cells and/or antibodies are introduced into the patient, for example in the form of healing sera. In contrast to active immunisation, passive immunisation has the task of healing an infection that has already taken place as quickly as possible or alternatively providing protection immediately against an infection with viruses. Various vaccination schemes for passive immunisation are known to the person skilled in the art, for example from passive immunisation against hepatitis A, hepatitis B or FSME. Vaccination schemes of this type can be adapted to specific retroviruses, such as, for example, HIV, feline leukaemia virus and others by routine experiments. The antibodies which are used for passive immunisation are preferably monoclonal antibodies. They are used, in particular, as constituent of a combination therapy.

All known and further constituents or components are familiar to the person skilled in the art and can undergo specific refinement for the teaching according to the invention in routine experiments.

Within the framework of the present invention, an ultrasmall silicon dioxide antigen conjugate which promotes an effective cellular immune response after vaccination is thus provided for the first time. The conjugate addresses a two-fold action mechanism in that it is capable both of specific targeting at antigen-presenting cells and also of simultaneous complement activation. The nanoparticles smaller than 50 nm have a targeting efficiency which is a multiple higher compared with large nanoparticles of the prior art. As a consequence of efficient transfer into the lymph vessels, the biophysical mechanism of interstitial flow can advantageously be utilised for the targeting of dendritic cells of the lymph nodes. Convection of the nanoparticles in this new transport route enables passive targeting, as a consequence of which complex cell-specific targeting is superfluous, but nevertheless a particularly large number of cells are reached since the dendritic cells are present in large number in lymph nodes. These properties form the basis for reliable recognition of dendritic cells of the lymph nodes—which includes the absence of crossreactivities (including targeting of peripheral dendritic cells)—and reproducible, reliable and complete phagocytosis into these antigen-presenting cells. The second advantageous property of the nanoparticles based on silicon dioxide, whose intrinsic adjuvant effect activates the immune system and in particular the complement system, takes effect at the target. While the strength of the activation is independent of the antigen selected, it can be modified via the particle size. The absence of additional assistants and/or modifications of the nanoparticle surface (for example polyhydroxylation) for the activation of the immune or complement system represents a significant simplification and cost saving.

The nanoparticles according to the invention are characterised by the inorganic, inert and biocompatible matrix material, which can be used, in particular, for prophylactic or therapeutic vaccination. The development of the nanoparticles comprising silicon dioxide/antigen conjugate presented here is likewise a highly promising strategy for improving the therapeutic index of cytotoxic active compounds. In particular, labile linking of the constituents ensures the liberation of the antigenic therapeutic agent in specific compartments of the body, meaning that a reduction in possible side effects can be expected. The nanoparticles are also distinguished by high pharmaceutical stability and are easy to handle, not least owing to their small size. The ultrafine nanodispersions comprising particles of monodisperse size are advantageously suitable for sterile filterability.

It goes without saying that this invention is not restricted to the specific methods, particles and conditions as described herein, since such things can be varied. It furthermore goes without saying that the terminology used here serves exclusively the purpose of description of particular embodiments and is not intended to restrict the scope of protection of the invention. As used here in the specification, including the appended claims, word forms in the singular, such as, for example, "a" or "the", include the equivalent in the plural, so long as the context does not specifically indicate otherwise. For example, the reference to "an antigen" includes a single antigen or a plurality of antigens, which may in turn be identical or different, or the reference to "a method" includes equivalent steps and methods which are known to the person skilled in the art.

The invention is explained in greater detail below with reference to non-limiting examples of specific embodiments. The examples should, in particular, be interpreted as not being restricted to the feature combinations specifically illustrated, but instead the illustrative features can in turn be freely combined so long as the object of the invention is achieved.

EXAMPLE 1

Production of Monodisperse Silicon Dioxide Particles

The production of the monodisperse silicon dioxide particles was carried out—as described in EP 0 216 278 B1—by hydrolysis of tetraalkoxysilanes in aqueous-alcoholic-ammoniacal medium, where firstly a sol of primary particles is produced, and the $SiO_2$ particles obtained are subsequently brought to the desired particle size by continuous metering-in of tetraalkoxysilane in a controlled manner corresponding to the extent of reaction. The production of 50 g of $SiO_2$ particles having a size of 25 nm requires, for example, 1.2 l of EtOH as solubiliser, 860 ml of deionised water, 167 ml of tetraethyl orthosilicate (TEOS) and 28.5 ml of 25% aqueous ammonia solution.

The spherical silicon dioxide particles were determined by means of dynamic lightscattering measurements using a Zetasizer Nano ZS (Malvern Instruments, Herrenberg, Germany). The Malvern-PDI (polydispersity index) having values <0.1 showed a monodisperse distribution. FIG. 1 depicts the particle size and morphology by means of an SEM photomicrograph.

EXAMPLE 2

Preparation of the OVA Peptide Fragment SIINFEKL having an N-Terminal Alkyne Group The peptide was constructed on a rink amide resin by means of Fmoc chemistry. N-alpha-Fmoc-protected amino acids having suitable side-chain protecting groups were employed. The solvent used was N-methylpyrrolidone. Firstly, the peptide chain was built up in an automatic synthesiser (Applied Biosystems Model ABI 433 A). After completion of the sequence, the terminal Fmoc protecting group was cleaved off. The polymer was coupled manually to the alkynecarboxylic acid in a syringe. It was carefully washed with DMF, followed by dichloromethane and methanol, and the resin was dried in vacuo overnight. For the cleaving off and deprotection, 5 ml of a mixture of TFA/H2O/phenol/triisopropylsilane (37:1:1:1) were added to the resin, and the mixture was shaken at room temperature for 2 h. The TFA solution was transferred into a centrifuge tube and precipitated by slow addition of diethyl ether at 4° C., centrifuged off, washed twice by addition of diethyl ether, dried and taken up in 2 ml of H2O/acetonitrile (1:1 v/v). The purification was carried out by RP-HPLC using an RP-select B column (150×10 mm) with a gradient from 0% of B—100% of B in 7.5 min (A=H2O and B=acetonitrile, both comprising 0.1% of TFA), flow rate=10 ml/min. The homogeneity and identity of the purified product was confirmed by analytical HPLC and mass spectrometry. After RP-HPLC purification, the peptide was lyophilised.

EXAMPLE 3

Functionalisation of the Silicon Dioxide Particles with 3-bromopropyltrimethoxysilane 1 g of the $SiO_2$ particles (25 nm) produced in Example 1 were suspended in an ethanol/water mixture (100 ml; 4:1), and 0.3 ml of 25% aqueous ammonia solution was added. 0.25 ml of 3-bromopropyltrimethoxysilane (ABCR, Karlsruhe, Germany), dissolved in 10 ml of ethanol, was subsequently slowly added dropwise via a dropping funnel, and the mixture was heated under reflux for about 20 h. The reaction mixture was cooled to room temperature, and the $SiO_2$ particles were washed 5× with an ethanol/water mixture (4:1). All washing steps were carried out by means of centrifugation for 10 minutes at 9000×g and 20° C. in a temperature-controlled centrifuge in 50 ml reaction vessels and by means of resuspension of the particles using an ultrasound finger.

EXAMPLE 4

Reaction of the Functionalised Silicon Dioxide Particles with Sodium Azide

The $SiO_2$ particles functionalised with 3-bromopropyltrimethoxysilane in the third example were redispersed in 80 ml of dimethyl sulfoxide (DMSO), 1 g of sodium azide and 100 mg of tetrabutylammonium bromide were added, and the mixture was stirred at 80° C. for 40 hours. 200 ml of deionised water were subsequently added, and the particles were isolated by means of an ultrafiltration method using a membrane with a retention capacity of 10 kDa (Millipore, Bedford, USA) and washed with 600 ml of deionised water.

EXAMPLE 5

Linking of the OVA Peptide Fragment SIINFEKL to the Functionalised $SiO_2$ Particles The azide-$SiO_2$ particles produced in the fourth example were resuspended in 40 ml of acetonitrile, the OVA peptide fragment from Example 1 (SIINFEKL-alkyne), diisopropylethylamine (DIPEA) and copper(I) iodide were added, and the mixture was stirred at room temperature for about 20 h. 100 ml of deionised water were added to the suspension, the product was isolated by means of ultrafiltration via a 10 kDa membrane (Millipore, Bedford, USA) and washed with 200 ml of deionised water and 50 ml of aqueous EDTA solution.

EXAMPLE 6

Testing of the Silica Nanoparticles for in-vivo Adjuvant Activity Using PBL Phenotypes (Peripheral Blood Lymphocytes) as Read-out The investigations were carried out on C57B1/6 mice. The animals were divided into 3 groups (2 mice per group) which were administered either PBS (phosphate buffered saline), LPS (lipopolysaccharide) or silica nanoparticles (25 nm). PBS served as control and LPS as reference (TLR4 agonist) benchmarked against the silica nanoparticles with respect to their adjuvant activity.

In the experiment, unmodified silica nanoparticles having a size of 25 nm which were produced by the method described in Example 1, dialysed and subsequently sterile-filtered were investigated. The silica dispersion was subsequently investigated for endotoxins in order to ensure that the read-out of the animal experiment would not be falsified by endotoxin contamination of the nanoparticles. The endotoxin concentration in the nanoparticle dispersion investigated is below the maximum level recommended by Ph. Eur. for liquid, parenteral formulations of 0.5 IU/ml.

100 μl of each of the test solutions or dispersion was administered s.c. (subcutaneously) to the animals in the flank. The nanoparticle dispersion comprised 450 μg of silica nanoparticles in 100 μl of PBS. As reference, 10 μg/mouse of LPS was administered.

Figure 2A:
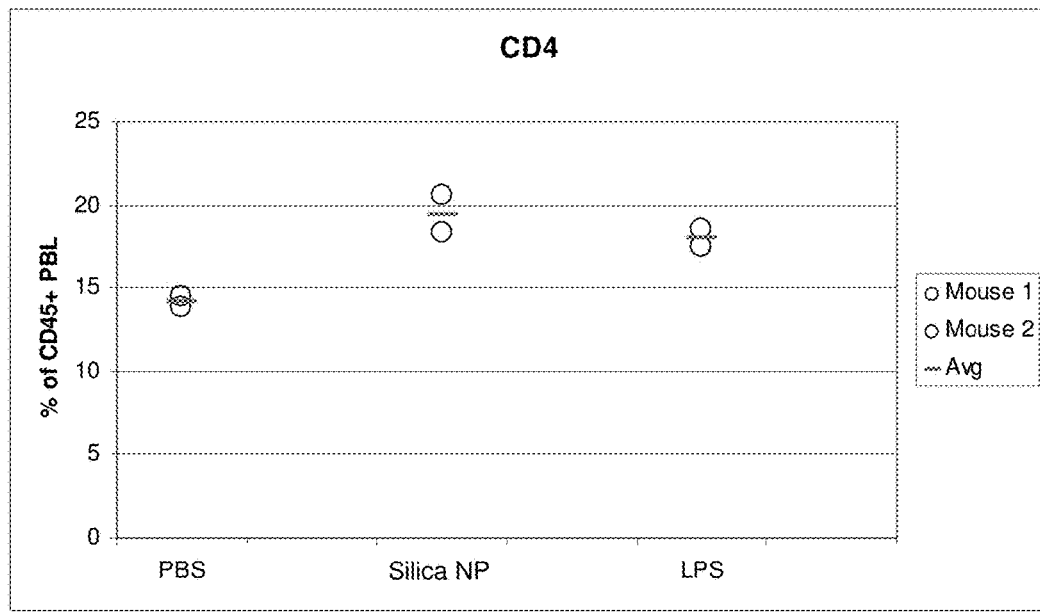
FIGS. 2a-2c plot the percentage proportion of the four PBL subpopulations CD4 (FIG. 2a), CD8 effector (FIG. 2b), CD11b+ and CD11c+(DC) (FIG. 2c) with respect to the total PBL population in the mice treated in Example 7.
Figure 2B:
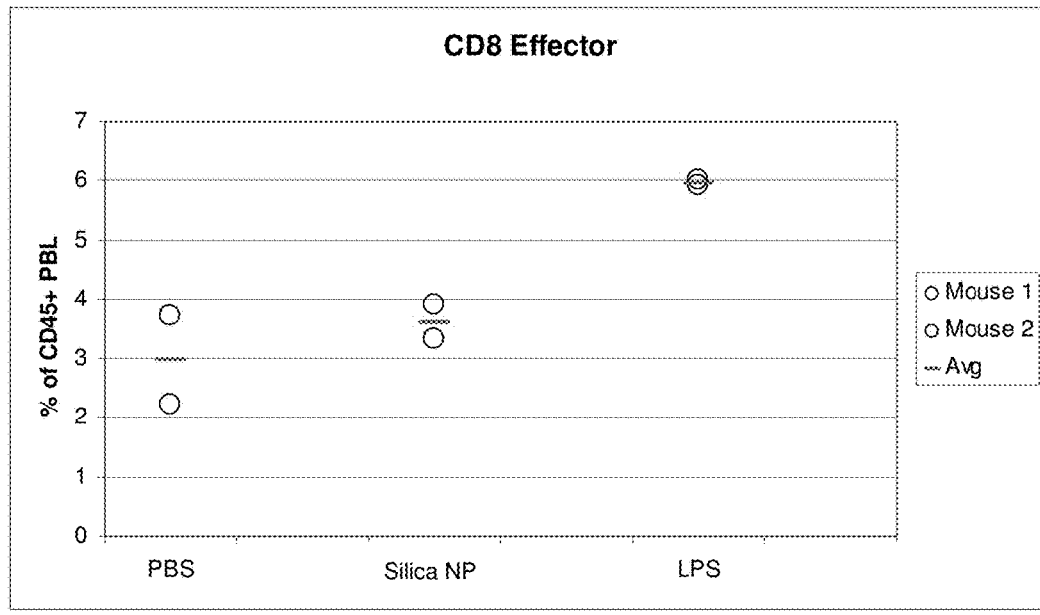
Figure 2C:
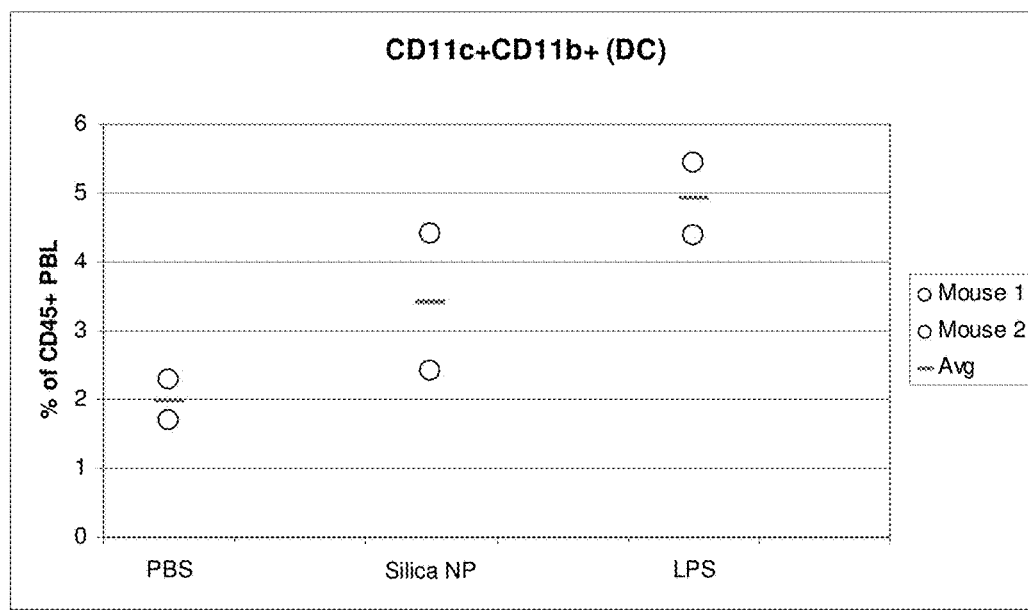

75-100 μl of peripheral blood/mouse was taken by retro-orbital bleeding by means of a heparinised capillary tube and collected in heparinised Eppendorf cups. The blood samples were labelled with various detection cocktails. The percentage distribution of immunologically relevant PBL phenotypes was subsequently determined by means of FACS (fluorescence activated cell sorting). In FIGS. 2a-2c, the percentage proportion of the four PBL subpopulations CD4 (FIG. 2a), CD8 effector (FIG. 2b), CD11b$^+$ and CD11c± (DC) (FIG. 2c) with respect to the total PBL population is plotted. The data confirm that, after administration of the silica nanoparticles, the number of immunologically important T-cells and dendritic cells was increased compared with the vehicle control PBS, which indicates an adjuvant effect of the silica nanoparticles.

EXAMPLE 7

$^{99m}$Tc Labelling of Silica Nanoparticles in Water

The nanoparticle solution (25 nm, solids content 9.0 mg/ml) was filtered through a MILEX-GV 0.22 μm filter unit before use. 50 μl of silica nanoparticles were added to $^{99m}$Tc (132 MBq in 40 μl), and the solution was mixed. 2 μl of an SnCl$_2$ solution (0.1% of SnCl$_2$ dihydrate in 10 mM HCl) were then added, and the solution was mixed again. After about 2 min, 150 μl of 0.5 M phosphate buffer pH 8 were added, and the solution was transferred into a Millipore Microcon Ultracel YM-100 centrifugal filter device and centrifuged at 13,000 rpm for 3 min. The filter was washed twice with 200 μl of 0.5 M phosphate buffer pH 8 each time. The total filtrate comprised 46.84 MBq of $^{99m}$Tc. 69.8 BMq of $^{99m}$Tc remained in the filter. The particles in the filter were suspended twice in 200 μl of 0.5 M phosphate buffer pH 8 each time and recovered by rotation of the filter and brief centrifugation. A particle suspension labelled with 28 MBq of $^{99m}$Tc was obtained. The particle suspension obtained was subsequently used for the animal experiment.

EXAMPLE 8

In-vivo Imaging of the $^{99m}$Tc-labelled Silica Nanoparticles

Figure 3:
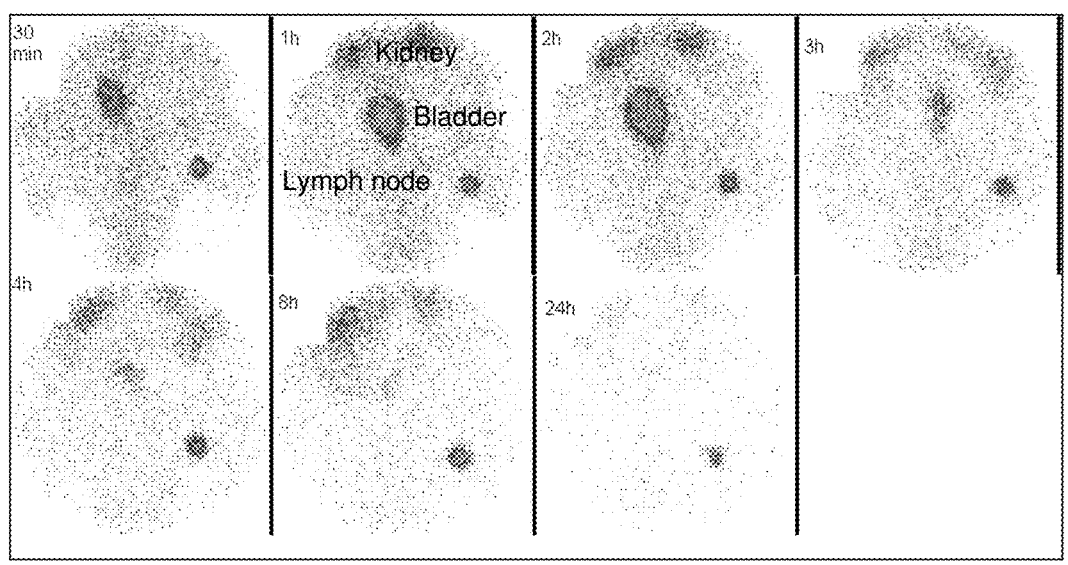
FIG. 3 shows gamma camera scintigraphy of the accumulation in the lower body of the rats treated in Example 8 at various times.

The particles were labelled as described in Example 7. Non-invasive imaging of the migration in the sentinel lymph nodes was subsequently carried out. For this purpose, female Wistar rats weighing about 400-500 g were anaesthetised by means of inhalation anaesthesia using isoflurane. The animals were given a subcutaneous injection of a clear suspension of the radiolabelled particles comprising 10-20 MBq of $^{99m}$Tc into one of the two hind paws. The animals, still under anaesthesia, were subsequently investigated by means of scintigraphy. For this purpose, the accumulation in the lower body of the animals at various times was displayed using a gamma camera. The kinetics of these photographs shows a significant accumulation of the particles in the lymph nodes leading away from the hind paw (see FIG. 3). These are the sentinel lymph nodes. In addition, a transient accumulation in the kidneys and bladder is evident. By contrast, the accumulation in the lymph node is continuous over 24 h. Migration rates of about 1% of the administered dose were observed. As control experiment, the analysis of the migration of $^{99m}$Tc-labelled NanoAlbumon, a commercially available colloid preparation for the imaging of the sentinel lymph node, was carried out. The accumulation of this substance was comparable to that of the silica particles. By means of a further control experiment, in which free $^{99m}$Tc was administered by subcutaneous injection into one of the two hind paws of female Wistar rats, it was ensured that free $^{99m}$Tc does not accumulate in the lymph node.

It was thus shown that the silica nanoparticles are able to target the lymph nodes, via which activation of the immune system can take place.

The following examples relate to pharmaceutical preparations.

EXAMPLE A

Injection Vials

A solution of 100 g of nanoparticles and 5 g of disodium hydrogenphosphate in 3 l of bidistilled water is adjusted to pH 6.8 using 2 N hydrochloric acid, sterile filtered, transferred into injection vials, lyophilised under sterile conditions and sealed under sterile conditions. Each injection vial contains 5 mg of nanoparticles.

EXAMPLE B

Suppositories

A mixture of 20 g of nanoparticles with 100 g of soya lecithin and 1400 g of cocoa butter is melted, poured into moulds and allowed to cool. Each suppository contains 20 mg of nanoparticles.

EXAMPLE C

Solution

A solution is prepared from 1 g of nanoparticles, 9.38 g of NaH$_2$PO$_4$*2H$_2$O, 28.48 g of Na$_2$HPO$_4$*12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of nanoparticles are mixed with 99.5 g of Vaseline under aseptic conditions.

EXAMPLE E

Tablets

A mixture of 1 kg of nanoparticles, 4 kg of lactose, 1.2 kg of potato starch, 0.2 kg of talc and 0.1 kg of magnesium stearate is pressed to give tablets in a conventional manner in such a way that each tablet contains 10 mg of nanoparticles.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of nanoparticles are introduced into hard gelatine capsules in a conventional manner in such a way that each capsule contains 20 mg of the nanoparticles.

EXAMPLE H

Ampoules

A solution of 1 kg of nanoparticles in 60 l of bidistilled water is sterile filtered, transferred into ampoules, lyophilised under sterile conditions and sealed under sterile conditions. Each ampoule contains 10 mg of nanoparticles.

EXAMPLE I

Inhalation Spray 14 g of nanoparticles are dissolved in 10 l of isotonic NaCl solution, and the solution is introduced into commercially available spray vessels with a pump mechanism. The solution can be sprayed into the mouth or nose. One spray shot (about 0.1 ml) corresponds to a dose of about 0.14 mg.

The invention claimed is:

1. A method for providing an adjuvant immune response, comprising administering nanoparticles of silicon dioxide to a patient in need thereof, wherein the nanoparticles have a size of at least 5 nm up to 150 nm.

2. The method of claim 1, wherein the nanoparticles have a size of 5 to 50 nm.

3. The method of claim 1, wherein the nanoparticles are monodisperse.

4. The method of claim 3, wherein the nanoparticles are non-porous.

5. The method of claim 1, wherein the nanoparticles are administered parenterally.

6. The method of claim 1, wherein the nanoparticles are passively targeted at antigen-presenting cells.

7. The method of claim 1, wherein the nanoparticles are targeted with a targeting efficiency that is adjusted via the size of the nanoparticles.

8. The method of claim 1, additionally comprising administering an antigen.

9. The method of claim 8, wherein the antigen is attached to a surface functionality on the nanoparticles.

10. The method of claim 8, wherein neither the surface functionality nor the antigen is a major histocompatibility (MHC) molecule.

11. The method of claim 9, wherein the surface functionality is a linker to which the antigen is covalently bonded on nanoparticles.

12. The method of claim 8, wherein the antigen is targeted at antigen-presenting cells.

13. The method of claim 8, wherein the antigen is targeted at dendritic cells in lymph nodes.

14. The method of claim 9, wherein the surface functionality forms a zeta-potential to which the antigen is adsorbed on the nanoparticles.

15. The method of claim 1, for generating an immune response in a patient in need thereof.

16. The method of claim 1, for inducing a T-cell response, an antibody response or a dendritic cell maturation in a patient in need thereof.

17. The method of claim 1, wherein the nanoparticles are targeted at dendritic cells in lymph nodes.

18. The method of claim 1, wherein the nanoparticles are functionalized.

19. The method of claim 18, wherein neither the surface functionality nor the antigen is a major histocompatibility (MHC) molecule.

20. The method of claim 1, wherein the nanoparticles are multi-functionalized.

21. A process for the production of an adjuvant comprising nanoparticles of silicon dioxide, comprising:
(a) hydrolytically polycondensing tetraalkoxysilanes and/or organotrialkoxysilanes in a medium comprising water, at least one solubilizer and at least one amine or ammonia, whereby a sol of primary particles formed by nucleation is produced, and the resultant nanoparticles are subsequently brought to the desired particle size in a range from 5 to 150 nm, wherein further nanoparticle nucleation is prevented by continuous metering-in of a corresponding silane in a controlled manner corresponding to the extent of reaction, and
(b) converting the nanoparticles into a suitable dosage form together with at least one solid, liquid and/or semi-liquid vehicle or assistant.

22. The method of claim 21, further comprising functionalizing the surface of the nanoparticles with a surface functionality after step (a) and before step (b).

23. The method of claim 21, wherein the particle size is in a range from 5 to 50 nm.

24. Nanoparticles for parenteral use, comprising a matrix comprising more than 50% of silicon dioxide, where the particles have a size of 5 to 50 nm and at least one cleavable linker as surface functionality to which at least one antigen is covalently bonded.

25. A process for the production of nanoparticles according to claim 24 having the following steps:
(a) hydrolytic polycondensation of tetraalkoxysilanes and/or organotrialkoxysilanes in a medium which comprises water, at least one solubiliser and at least one amine or ammonia, where firstly a sol of primary particles is produced, and the resultant nanoparticles are subsequently brought to the desired particle size in a range from 5 to 50 nm in such a way that further nucleation is prevented by continuous metering-in of corresponding silane in a controlled manner corresponding to the extent of reaction,
(b) functionalisation of the surface with a cleavable linker as surface functionality, and
(c) covalent bonding of an antigen to the surface functionality of the nanoparticles.

26. A method for the targeting and liberation of antigens at/in antigen-presenting cells having the following steps:
(a) administering to a patient in need thereof nanoparticles of claim 24, wherein the matrix consists essentially of pure silicon dioxide, to antigen-presenting cells present in cell culture, tissue, organs or a mammal, (b) targeting of the antigens at antigen-presenting cells via the interstitial fluid by adjusting the targeting efficiency via the size of the nanoparticles, which are inversely proportional, whereby the nanoparticles are taken up into the antigen-presenting cells, and the antigens from the matrix of the nanoparticles are liberated in the endosome.

27. A vaccination method for therapy of diseases selected from the group consisting of infectious diseases, septic shock, tumours, cancer, autoimmune diseases, allergies and chronic and acute inflammation processes, wherein infectious diseases and septic shock resulting from such infections are selected from the group consisting of diseases caused by pathogenic viruses, bacteria, fungi and single-celled animals;

tumors or cancers are selected from the group consisting of cancer or tumour diseases of the ear-nose-throat region, mediastinal cavity, gastrointestinal tract, urogenital system, gynaecological system, endocrine system, lung, breast, skin, bone, soft-part sarcomas, mesotheliomas, melanomas, neoplasms of the central nervous system, paediatric cancer diseases or tumour diseases, lymphomas, leukaemias, paraneoplastic syndromes, metastases without known primary tumour (CUP syndrome), peritoneal carcinomatoses, immunosuppression-related malignancies, multiple myelomas and tumour metastases; and autoimmune diseases, allergies, and chronic and acute immune processes are selected from the group consisting of arthritis, autoimmune hepatitis, chronic gastritis, neurodermatitis, psoriasis, arthrosis, rheumatic diseases, rheumatoid arthritis, juvenile idiopathic arthritis, Crohn's disease, suppurative inflammation of the colon, diabetes, inflammatory bowel diseases, multiple sclerosis and allergic inflammations; and wherein an effective amount of the nanoparticles according to claim 24 is administered to a mammal in need of such a treatment.

28. A method for the activation of the immune system of a patient in need thereof and providing an adjuvant immune response, comprising parenterally administering, to a patient in need thereof, nanoparticles of silicon dioxide, where the nanoparticles have a diameter of 5 to 50 nm and are free of additional adjuvants.

* * * * *